United States Patent [19]
Tu et al.

[11] Patent Number: 6,024,742
[45] Date of Patent: Feb. 15, 2000

[54] ABLATION APPARATUS FOR TREATING HEMORRHOIDS

[76] Inventors: Lily Chen Tu; Hosheng Tu, both of 2151 Palermo, Tustin, Calif. 92782

[21] Appl. No.: 09/138,212

[22] Filed: Aug. 22, 1998

[51] Int. Cl.⁷ .................................................. A61B 17/36
[52] U.S. Cl. .............................. 606/41; 606/47; 606/49; 606/169; 607/101; 128/898
[58] Field of Search ........................... 606/41–52, 32–34, 606/167, 169, 170; 128/898, 11

[56] References Cited

U.S. PATENT DOCUMENTS

| | | | |
|---|---|---|---|
| 5,417,700 | 5/1995 | Egan | 606/144 |
| 5,458,596 | 10/1995 | Lax et al. | 606/31 |
| 5,709,224 | 1/1998 | Behl et al. | 128/898 |
| 5,863,290 | 1/1999 | Gough et al. | 606/41 |

FOREIGN PATENT DOCUMENTS

9732532  9/1997  WIPO ..................................... 606/41

Primary Examiner—David M. Ruddy

[57] ABSTRACT

A medical apparatus for treating the hemorrhoid, or reducing the dilatation of tubular cellular tissues, wherein an elongate tubular shaft comprises at least one extendible wire means disposed at its distal end portion of the shaft to form a cylindrical void and adapted to encircle the tubular cellular tissues with a RF energy therapy, and a means for pressing the wire means against the target tissue to effect the ablation and the pressure therapy for the tubular tissues.

12 Claims, 7 Drawing Sheets

ABLATION APPARATUS FOR TREATING HEMORRHOIDS

The present invention generally relates to improved medical apparatus and methods for treating vascular tissues, and more particularly, to such a medical apparatus and methods for treating hemorrhoids and cylindrical organs in a patient by delivering therapeutic RF energy to the specific lesion sites.

BACKGROUND OF THE INVETION

As a result of aging or under certain internal pressures, some tissue may start to become loosen or dilated. This is especially true to a vascular vessel or internal tubular organs. One method of reducing the size of cellular tissues in situ has been used in the treatment of many diseases, or as an adjunct to surgical removal procedures. This method applies appropriate heat to the tissues, and causes them to shrink and tighten. It is often less traumatic than surgical procedures and may be the only alternative method, wherein other procedures are unsafe or ineffective. Ablative treatment apparatus have an advantage because of the use of a therapeutic energy that is rapidly dissipated and reduced to a non-destructive level by conduction and convection, to other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the apparatus-to-tissues contact site to obtain the desired temperature for treating a tissue.

Hemorrhoid is a varicose dilatation of a vein of the superior or inferior hemorrhoidal plexus, resulting from a persistent increase in venous pressure. The external hemorrhoid is a varicose dilatation of a vein of the inferior hemorrhoidal plexus, situated distal to the pectinate line and covered with modified anal skin. The internal hemorrhoid is a varicose dilatation of a vein of the superior hemorrhoidal plexus, originating above the pectinate line, and covered by mucous membrane. A more serious case of hemorrhoid, prolapsed hemorrhoid, is an internal hemorrhoid that has descended below the pectinate line and protruded outside the anal sphincter. One of the worst cases, strangulated hemorrhoid, is an internal hemorrhoid which has been prolapsed sufficiently and for long enough time for its blood supply to become occluded by the constricting action of the anal sphincter.

Taylor in U.S. Pat. No. 5,578,047 teaches a hemorrhoid-removing apparatus. Tuffel in U.S. Pat No. 4,938,221 teaches a hemorrhoid inflammation-reducing apparatus. Bidoia in U.S. Pat. No. 5,203,863 teaches an instrument for the ligation of hemorrhoids. None of them discloses a medical apparatus by using a suitable energy to treat a dilated vein to shrink and tighten it. On the other hand, an alternative for hemorrhoid treatment is by surgically removing the dilated vein with a laser or other means. For a dilated vein, RF energy or other suitable energy can be applied for treating the tissues of the vascular walls, and causing them to shrink and tighten.

There is one major obstacle for a tubular or catheter-based RF ablation procedures. When contacting a catheter-based tubular apparatus against a tubular vessel, the contact surface is minimal so that the effectiveness is substantially compromised. Therefore, there is a need for an improved medical apparatus having the capability to encircling a tubular vessel using the radiofrequency energy to treat a dilated vein or tissue, such as hemorrhoids while simultaneously applying pressure therapy to the target tissue.

SUMMARY OF THE INVENTION

In general, it is an object of the present invention to provide a method and an improved medical apparatus for generating heat, to treat the hemorrhoids, vascular vessels, or other cylindrical organs, such as intestine, colon, ureter, uterine tube, and the like. It is another object of the present invention to provide a method and an apparatus for monitoring the temperature of the medical apparatus, and to control the temperature by utilizing a temperature control mechanism and/or algorithm. The location of the temperature sensor means is preferably at close proximity of the electrode means of the medical apparatus. It is still another object of this invention to provide a method and an apparatus for treating hemorrhoids, vascular walls, or tubular cellular tissues in a patient by applying appropriate pressure to the tissues.

Briefly, heat is generated by supplying a suitable energy source to an apparatus, which is comprised of at least one electrode means, in contact with the body tissues. A suitable energy source may consist of radiofrequency energy, microwave energy, ultrasonic energy, alternating current energy, or laser energy. The energy can be applied to the hemorrhoids, vascular walls, or cellular tissues through the electrode means. A DIP (dispersive indifferent pad) type pad or electrode, that contacts the patient, is connected to the Indifferent Electrode Connector on the RF generator. Therefore, the RF energy delivery becomes effective when a close circuit from a RF generator through a patient and returning to the RF generator is formed. When using an alternating current outlet, the generator should be grounded to avoid electrical interference. Heat is controlled by the power of the RF energy delivered and by the delivery duration. The standard RF energy generator means and its applications through the electrode means, to a patient are well known for those who are skilled in the art.

In an optional embodiment, means for generating vibration at the distal section comprises a motor mounted in the cavity of the handle, which has a rotatable motor shaft, an elongated connecting shaft having a first end, to which the distal end portion is connected, and a second end connected to the handle, a weight eccentrically mounted on the motor shaft with respect to the motor shaft axis, so as to rotate eccentrically, so that when the motor shaft rotates, the distal end portion of the apparatus vibrates.

In one embodiment, the apparatus comprises at least one electrode means, wherein the electrode means is composed of a deployable wire or plurality of wires. The deployed wires form an electrode to encircle the target tubular tissues/organs. The wires of the electrode assembly are connected to an external RF generating means through an electrical conductor. The contact surface of the electrode assembly to the target tissue is pre-shaped and/or maximized by either curving the contact surface or by pre-shaping the contacting wires in a concave fashion to encircle the round body of the hemorrhoids and the like. The wires of the electrode assembly are semi-compressible so that when the deployed wire is pressed against the tissues or the round surface of a hemorrhoid, an appropriate pressure is exerted onto the tissues while applying the RF energy therapy.

The method and medical apparatus of the present invention has several significant advantages over other known systems or techniques to treat the hemorrhoids or polyps. In particular, the apparatus system comprising the electrode assembly means, using RF energy as a heat source, in this invention and simultaneously applying pressure therapy to the tissues, results in a more efficient therapeutic effect, which is highly desirable in its intended application on the hemorrhoids or on other tubular organ ablation applications.

BRIEF DESCRIPTION OF TIE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
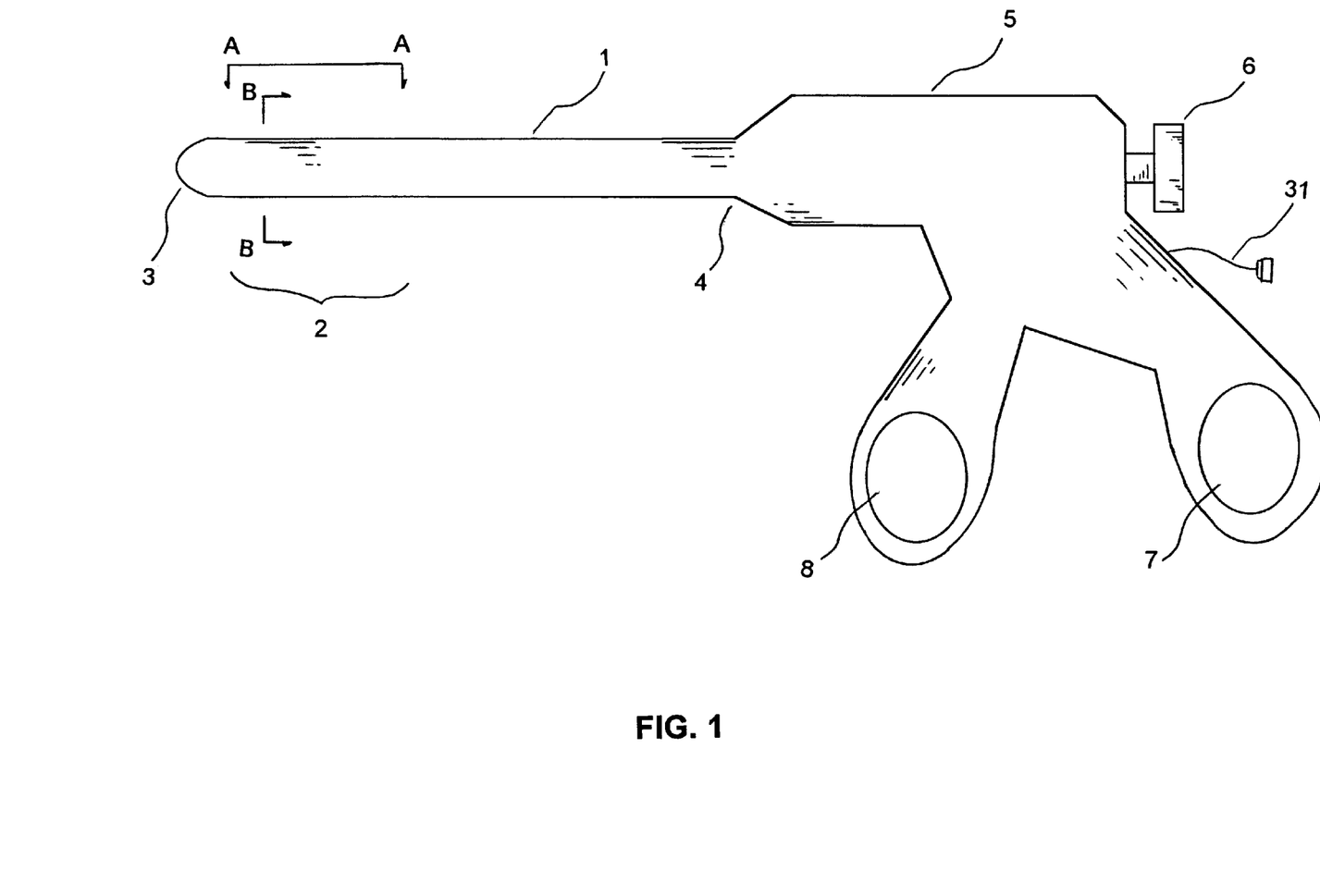
FIG. 1 is an over-all view of the medical apparatus, comprising a tubular shaft and a handle constructed in accordance with the principles of the present invention.

Referring to FIGS. 1 to 7, what is shown is an embodiment of the medical apparatus system, comprising simultaneously applying radiofrequency energy and applying a pressure therapy to treat the hemorrhoids, vascular vessels, polyps, or other tubular cellular tissues of a patient. As shown in FIG. 1, the medical apparatus in the form of an elongate tubular assembly comprises a tubular shaft 1 having a distal section 2, a distal end 3, a proximal end 4, and at least one lumen 15 extending therebetween. The tubular shaft 1 has at least one opening 9 at one side of the tubular shaft 1. In one embodiment, the openings 9 and 17 are preferred at the top side 20 of the apparatus to maximize the contact between the apparatus and the target tissue. A handle 5 is attached to the proximal end 4 of the tubular shaft 1, wherein the handle 5 has a cavity 34.

A deployable electrode assembly located inside one of the at least one lumens 15 of the tubular shaft 1 at its distal section 2. The electrode assembly comprises a concave-shaped shaft surface 20 and a plurality of extendible wires 12 and 16 extended from the appropriate side of the openings 9 and 17, respectively. A first extendible wire means has a wire end 10, wire body 12 and wire base 13, which is shaped to form one side of a cylindrical void when deployed. Similarly, a second extendible wire means comprises a wire end 11, wire body 16 and wire base 19. In one embodiment, the plurality of wire means is extended from the two openings 9 and 17 at the distal section 2 of the tubular shaft 1. The plurality of extended wires means along with the concave-shaped shaft surface 20 constitute the electrode assembly means of the present invention. In one embodiment, the tubular shaft 1 is semi-flexible and bendable, which is adapted to having a steering mechanism for the apparatus.

Figure 2A:
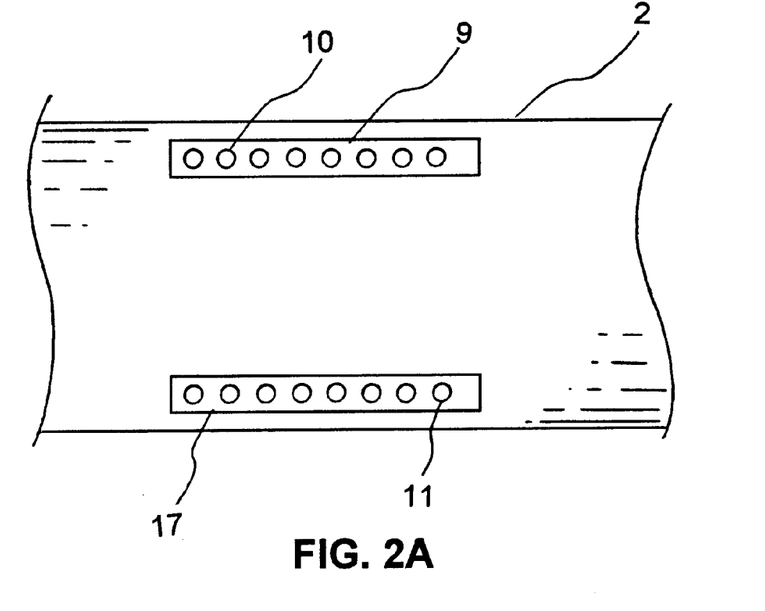
FIG. 2A is a top view of the distal end portion of the apparatus, including a plurality of openings at the top side of the tubular shaft for deploying the ablation wires.

FIG. 2A shows a top view of the distal end portion of the apparatus, including a plurality of openings 9 and 17 at the top side of the tubular shaft 1 for deploying the ablation wires. Under non-deployed state, the deployable wires are retracted inside the lumen of the distal end portion. The wire ends 10 and 11 are located just within the surface of the tubular shaft 1. In one embodiment, the axial side of the opening 9 or 17 of the distal section 2 extends all the way to the distal end 3.

Figure 2B:
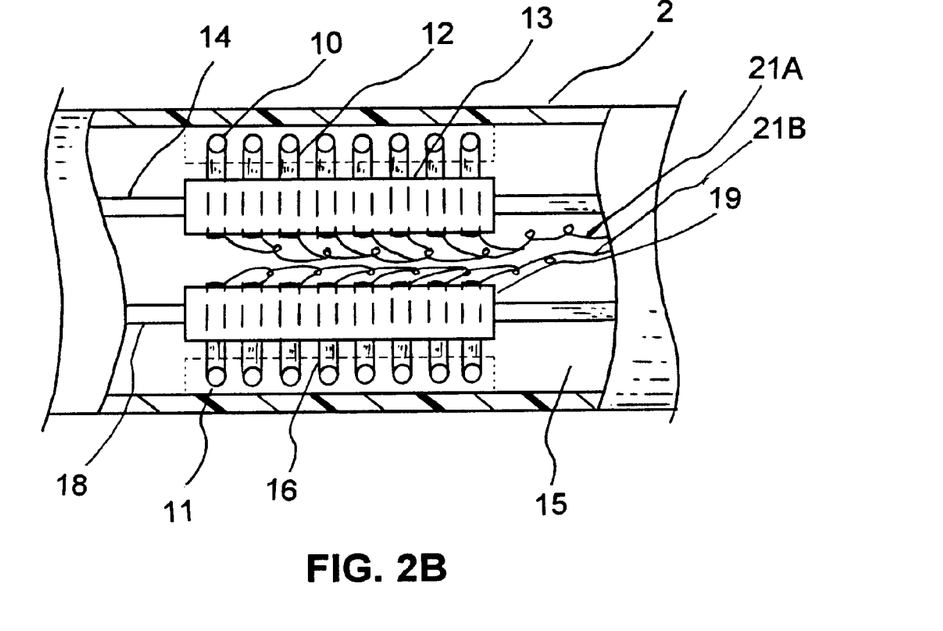
FIG. 2B is a top cross-sectional view of the distal end portion of the apparatus, having an electrode assembly comprising a plurality of wire deployment means along with their corresponding openings at the top side of the tubular shaft.

FIG. 2B shows a top cross-sectional view of the distal end portion 2 of the apparatus, including a plurality of wire deployment means 13 and 19 along with their corresponding openings 9 and 17 at the top side 20 of the tubular shaft 1. The extendible wire means comprises a plurality of wires, each wire has a wire end 10 or 11, wire body 12 or 16, and wire base 13 or 19, wherein the wire base is rotatable to deploy the wire 12 out of the opening 9 and retract the wire back inside the lumen 15 of the tubular shaft 1. The deployment operation for each deployable wire means is controlled by a controller 6A or 6B located at the proximal end of the handle 5, wherein the rotatable wire base 13 or 19 is connected to the controller through a connecting shaft 14 or 18 and a connecting joint 32A or 32B. An insulated electrical conductor means 21A or 21B passes through the lumen 15 of the shaft 1 and is connected to the electrode means of the electrode assembly. The other end of the electrical conductor means is connected to an external RF generator through the connector 31.

Figure 3:
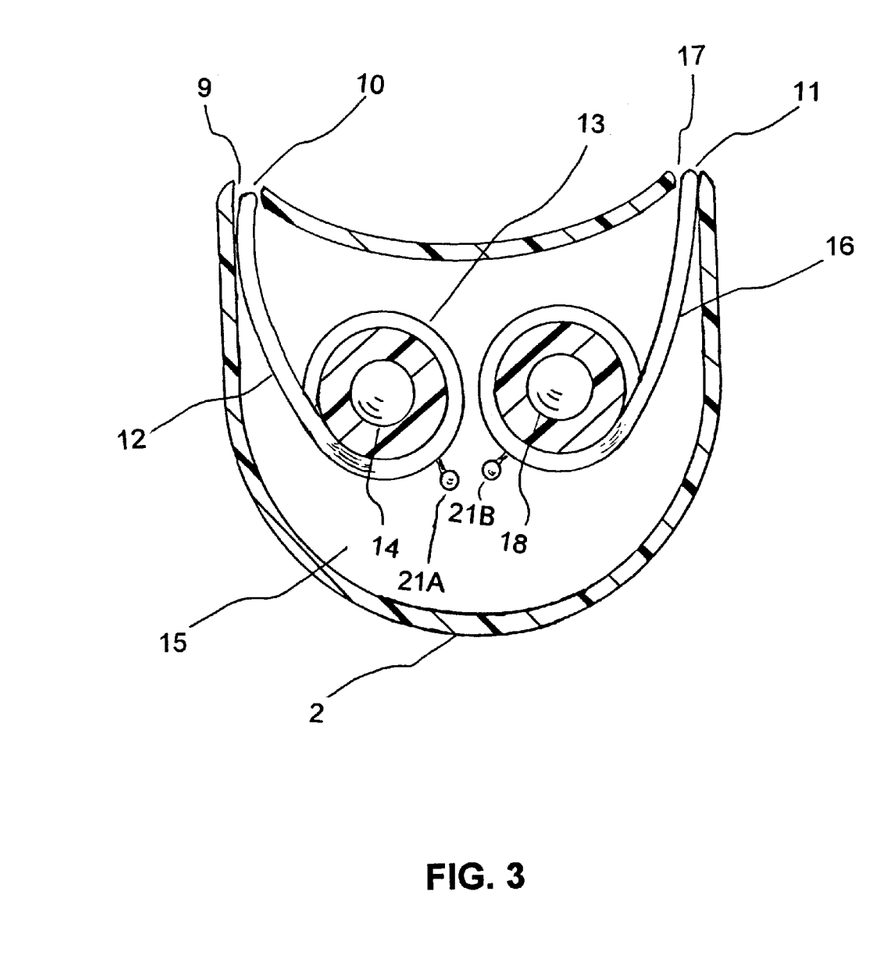
FIG. 3 is a front cross-sectional view of the deployable electrode assembly at the non-deployed state.

FIG. 3 shows a front cross-sectional view of the deployable electrode assembly at the non-deployed state. The wire end 10 or 11 of the deployable wire means stays within the lumen 15 of the shaft 1. The deployment operation is initiated at the wire base 13 or 19 and is controlled by a controller 6A or 6B through a connecting shaft 14 or 18. The wire means is connected to a conducting wire 21A or 21B for relaying the RF current to the electrode means of the electrode assembly.

Figure 4:
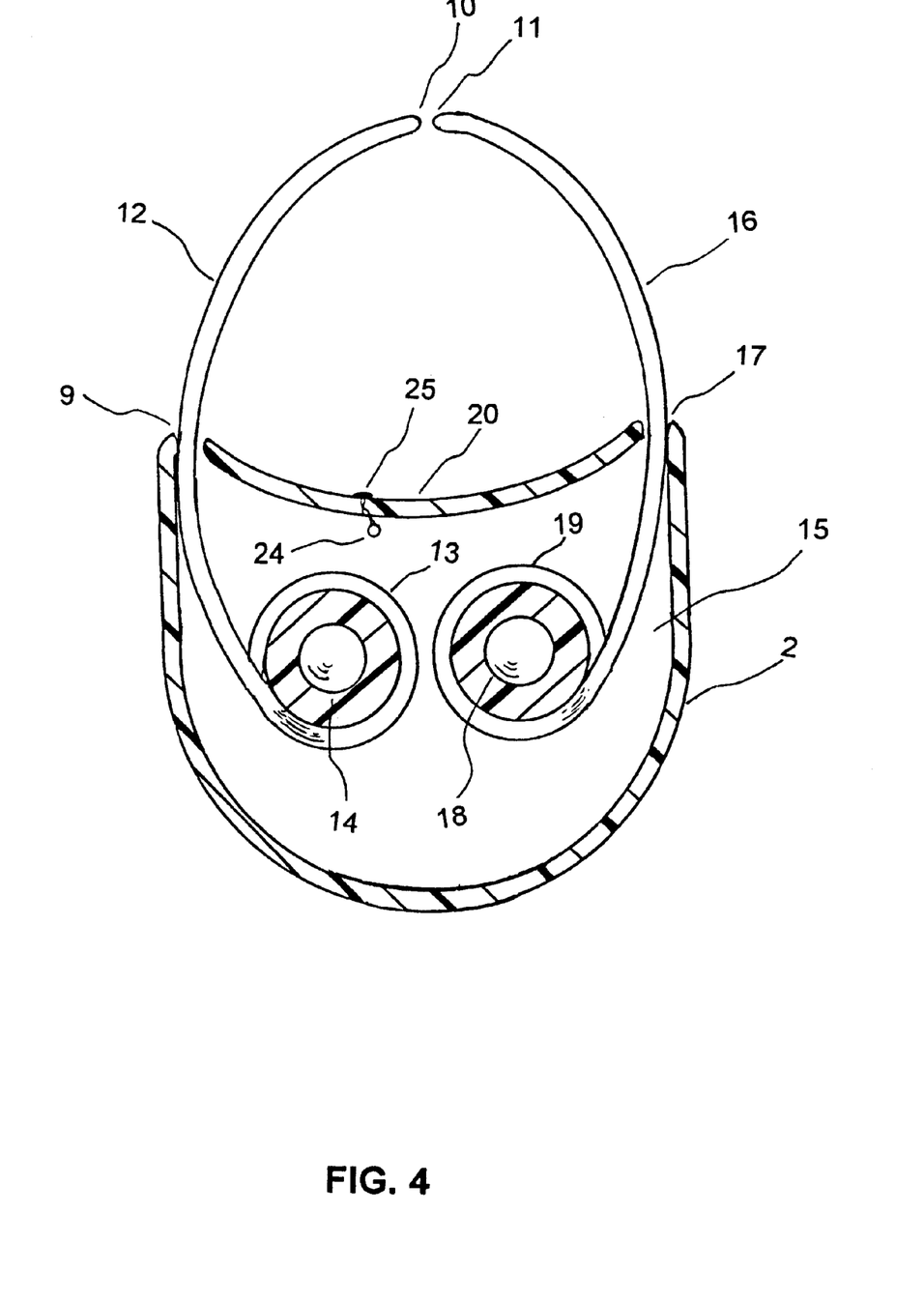
FIG. 4 is a front cross-sectional view of the deployable electrode assembly at the deployed state.

FIG. 4 shows a front cross-sectional view of the deployable electrode assembly at a deployed state. The deployed wire means 12 or 16 and the base surface 20 of the tubular shaft at its distal section 2 forms a cylindrical void and is adapted to receive or cover a tubular organ or hemorrhoid and maximize the contact with the target tissue for RF energy treatment. This portion of the top surface 20 of the tubular shaft 1 is made of conductive material, which is also connected to the RF energy source through an insulated electrical conductor. The shape of the cylindrical void thus formed can be designed by pre-shaping the wire means 12 and 16 and the concave-shaped top surface 20 of the tubular shaft 1. Other portion of the shaft and surface of the apparatus is not conductive.

Figure 5:
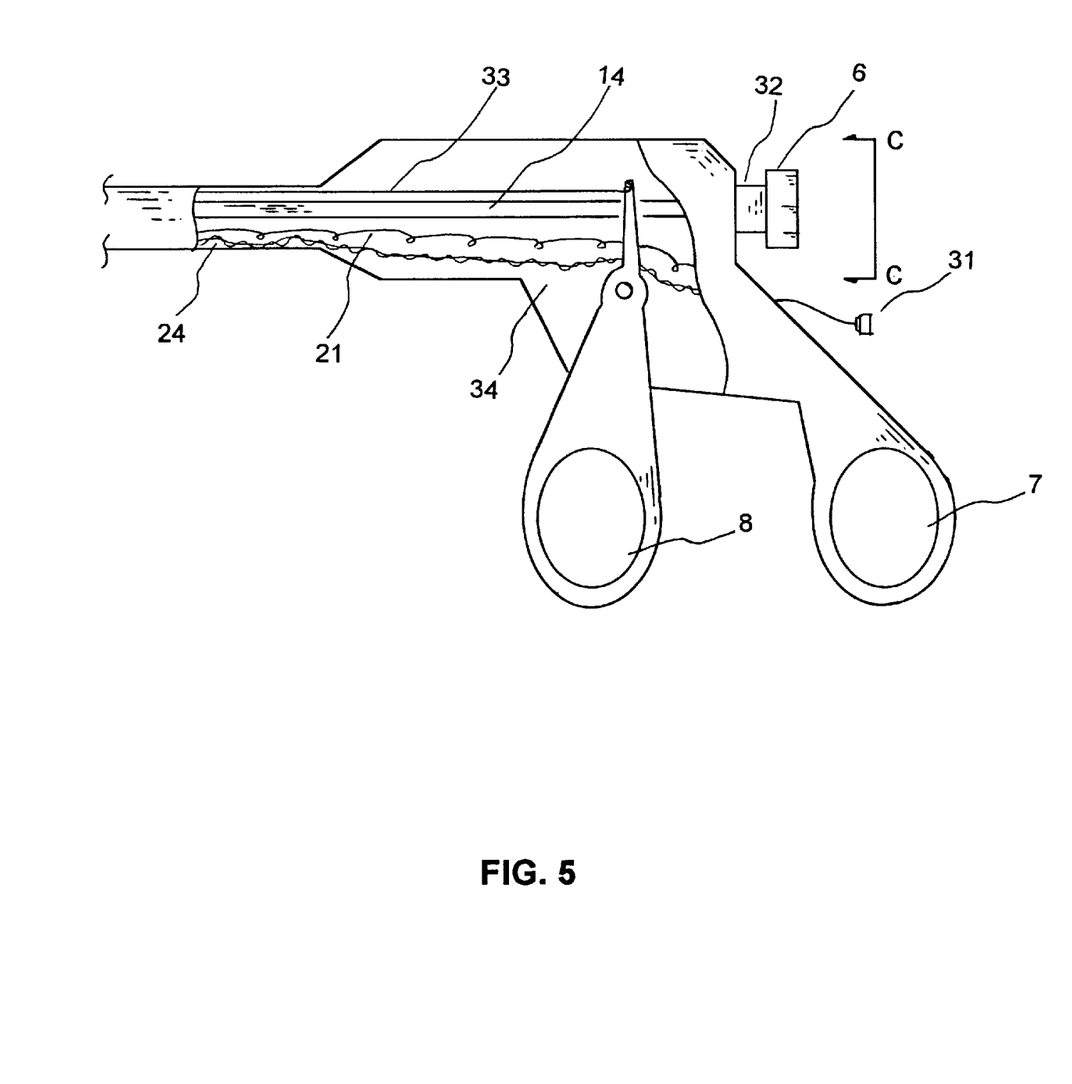
FIG. 5 is a cross-sectional view of the handle of FIG. 1.
Figure 6:
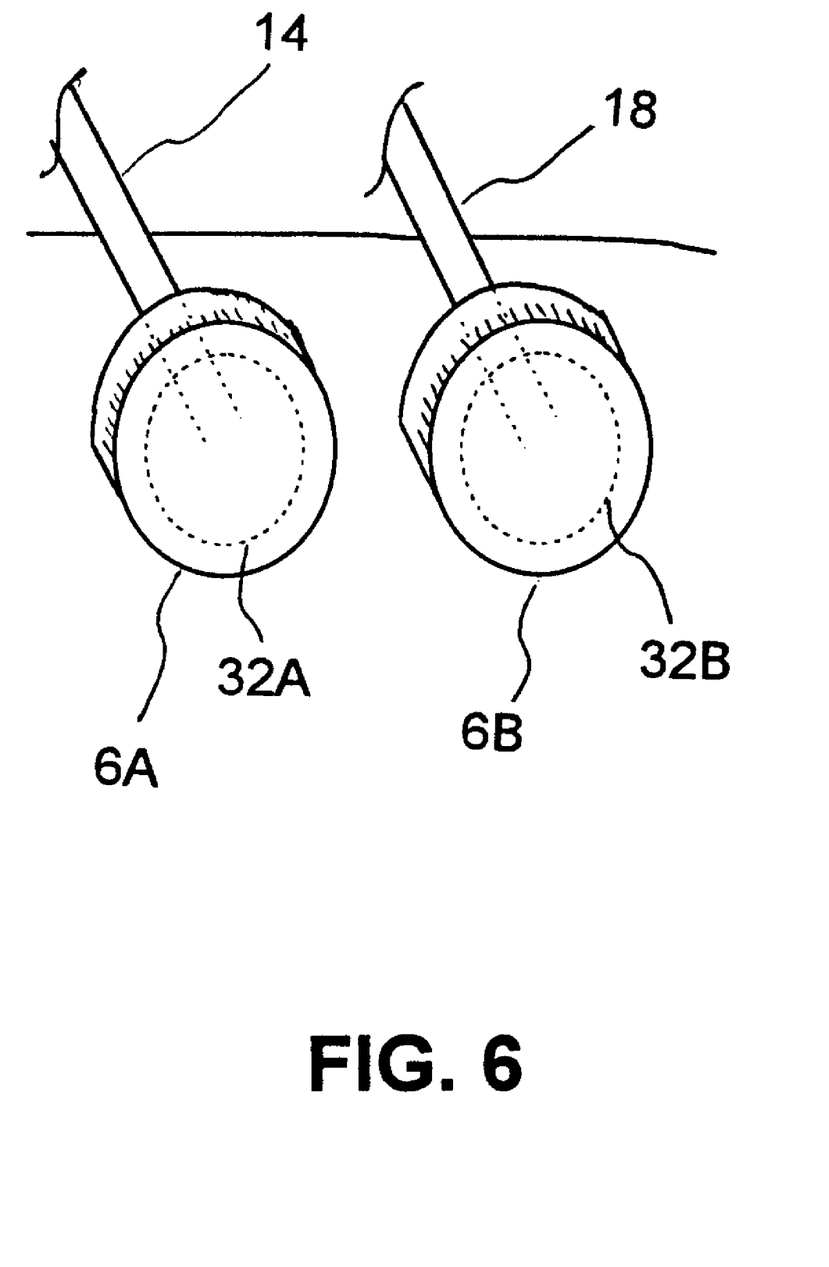
FIG. 6 is a controller for the deploying mechanism of the electrode assembly at the proximal end of the handle.

FIG. 5 shows a cross-sectional view of the handle 5 of the present invention. The handle 5 comprises a cavity 34 and holders 7 and 8 for the thumb and finger so that the distal portion 2 of the elongate tubular shaft 1 can be steered with ease. The RF electricity of the electrical conductor 21 is connected to an external RF energy source through the connector 31. The connector 31 comprises several pins for connecting an electrical conductor 21 to external instruments, such as a RF generator, and a temperature sensing wire 24 to a temperature control mechanism.

In one embodiment, at least one temperature sensing means 25 is disposed at close proximity of the shaft surface 20. Insulated temperature sensor wire means 24 passes from the temperature sensing means 25 at the shaft surface, to an external temperature control mechanism through the outlet connector 31. The RF energy delivery is controlled by using the measured temperature from the temperature sensing means 25, through a closed-loop temperature control mechanism and/or algorithm. When the measured temperature rises to the preset high-limit point, the temperature control mechanism sends out a signal to cut off the RF energy supply. In a similar manner, when the measured temperature drops to the preset low-limit point, the temperature control mechanism sends out a signal to activate the RF energy supply.

The apparatus is also optionally equipped with a steering mechanism at the handle. One end of a steering wire 33 is secured at the end portion of the finger holder 8, wherein the other end of the steering wire is secured to a remote point of the tubular shaft 1 at its distal tip portion 2. By releasing the finger holder 8 relative to the thumb holder 7, the steering wire 33 exerts tension to the distal tip section to deflect the tip section. The steering mechanism and its construction in a medical apparatus is well-known to those who are skilled in the art.

Figure 7:
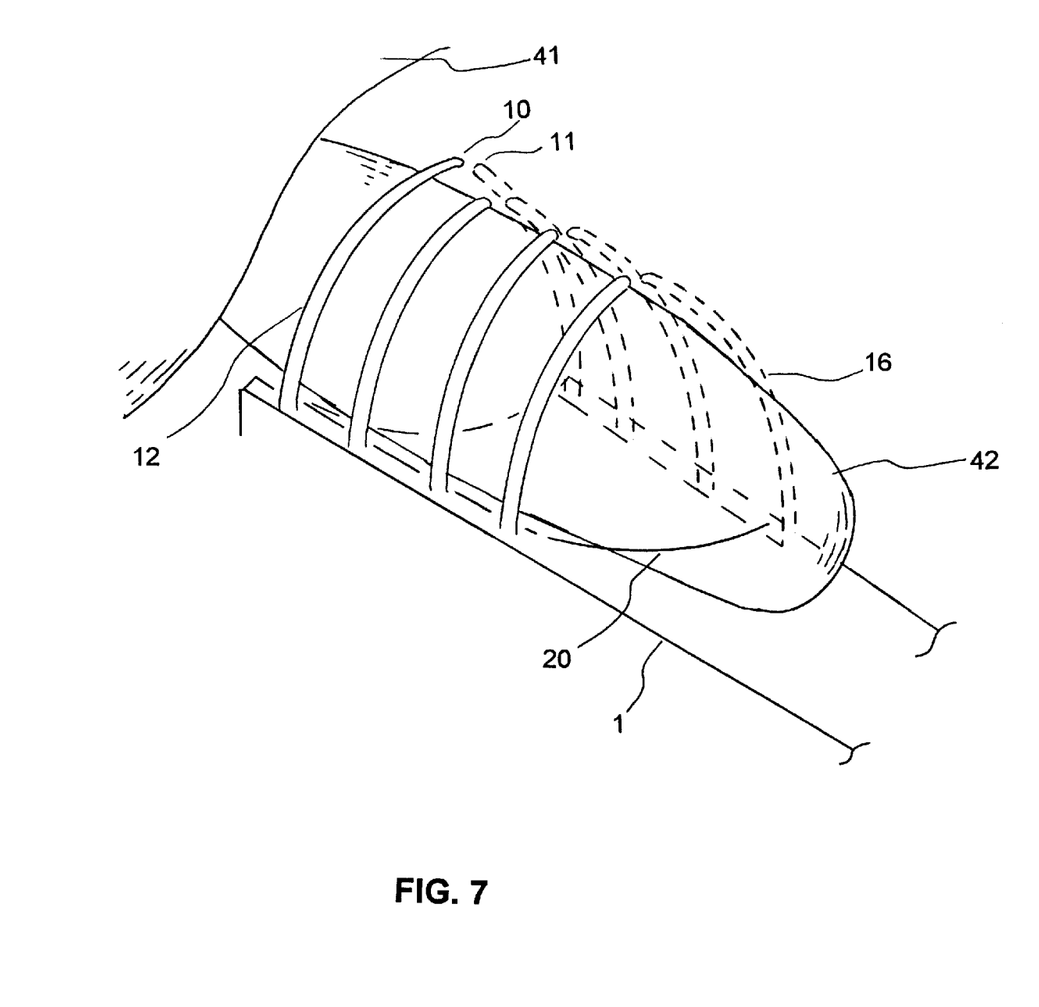
FIG. 7 shows a perspective view of a tubular organ being treated by the medical apparatus of the present invention.

FIG. 7 shows a perspective view of a prolapsed hemorrhoid or a tubular organ being treated by the medical apparatus of the present invention. For illustrative purposes, the hemorrhoid 42 is protruded from its base tissue 41 and hangs loose within the rectum. Two wires means 12 and 16 with a plurality of parallel wires are deployed to form a cylindrical void with the shaft surface 20 as the other side of the cylindrical void to encircle the prolapsed hemorrhoid. By deploying the wires means further, the hemorrhoid is intimately enclosed by the electrode assembly of the present invention under certain pressure.

During procedures, the medical apparatus is inserted into the body of a patient through natural opening or a surgical hole. A method of treating a tubular organ of a patient, the method comprising: (a) placing a medical apparatus system against the tubular organ of the patient, wherein the medical apparatus comprises a tubular shaft having a distal section, a distal end, a proximal end, and at least one lumen extending therebetween, wherein the distal section has at least one opening at one side of the tubular shaft; a handle attached to the proximal end of the tubular shaft, wherein the handle has a cavity; a deployable electrode assembly located inside one of the lumens of the tubular shaft at its distal section, wherein the electrode assembly comprises a concave-shaped shaft surface at the same side of the opening and a plurality of extendible wires shaped to form a cylindrical void when deployed, and wherein the plurality of wires is extended from the at least one opening at the distal section of the tubular shaft; (b) deploying the electrode assembly to encircle the tubular organ; and (c) applying RF energy to the tissues encircled under the electrode assembly to effect treatment of the tubular organ.

As an alternative illustration, a method of treating a hemorrhoid of a patient, the method comprising the steps of: (a) inserting a medical apparatus through the anal canal into the rectum of a patient, wherein the medical apparatus comprises a tubular shaft having a distal section, a distal end, a proximal end, and at least one lumen extending therebetween, wherein the distal section has at least one opening at one side of the tubular shaft; a handle attached to the proximal end of the tubular shaft, wherein the handle has a cavity; a deployable electrode assembly located inside one of the lumens of the tubular shaft at its distal section, wherein the electrode assembly comprises a concave-shaped shaft surface at the same side of the opening and a plurality of extendible wires shaped to form a cylindrical void when deployed, and wherein the plurality of wires is extended from the at least one opening at the distal section of the tubular shaft; (b) deploying the electrode assembly to encircle the hemorrhoid; and (c) applying RF energy to the hemorrhoid encircled under the electrode assembly to effect treatment of the hemorrhoid.

The external RF energy generator means has the capability to supply RF energy by controlling the time, power, and temperature through an optional separate closed-loop temperature control means. The patient is connected to the RF generator means through a DIP electrode to form a closed-loop current system. Therefore, RF energy is applied and delivered to the targeted hemorrhoid region, through the electrode means of this invention. The radiofrequency energy current in this invention is preferably within the range of 50 to 2,000 kHz. The frequency of the vibration of the medical apparatus in this invention is preferably within the range of 60 to 1000 cycles per minute. By simultaneously applying RF energy to the electrode and by applying the pressure therapy, the hemorrhoid can be treated.

In a particular embodiment, the material for the electrode means of this invention consists of conductive metals such as platinum, iridium, gold, silver, stainless steel, Nitinol, or an alloy of these metals.

From the foregoing description, it should now be appreciated that a apparatus system for the tubular organs, hemorrhoids, and the treatment of vascular tissues, comprising a suitable energy source and a pressure therapy has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method of treating a tubular organ of a patient, the method comprising:
    (a) placing a medical apparatus system against the tubular organ of the patient from an exterior side of said tubular organ, wherein the medical apparatus comprises a tubular shaft having a distal section, a distal end, a proximal end, and at least one lumen extending therebetween, wherein the distal section has at least one opening at one side of the tubular shaft; a handle attached to the proximal end of the tubular shaft, wherein the handle has a cavity; a deployable electrode assembly located inside one of the lumens of the tubular shaft at its distal section, wherein the electrode assembly comprises a concave-shaped shaft surface at the same side of the opening and a plurality of extendible wires shaped to form a cylindrical void when deployed, and wherein the plurality of wires are extended from the at least one opening at the distal section of the tubular shaft;
    (b) deploying the electrode assembly to encircle the tubular organ from externally around said tubular organ; and (c) applying RF energy to the tissues encircled internally under the electrode assembly to effect treatment of the tubular organ.

2. The method of treating a tubular organ of a patient as in claim 1, the method further comprising the medical apparatus system having the shaft surface and the extendible wires for the cylindrical void being made of conductive material.

3. The method of treating a tubular organ of a patient as in claim 1, the method further comprising the medical apparatus system having a steering mechanism adapted for deflecting the distal section of the medical apparatus.

4. The method of treating a tubular organ of a patient as in claim 1, the method further comprising the medical apparatus system comprising at least one temperature sensor, wherein the temperature sensor is disposed at close proximity of the electrode assembly of the medical apparatus system.

5. The method of treating a tubular organ of a patient as in claim 4, the method further comprising the medical apparatus system comprising a temperature control means, wherein the temperature measured from the temperature sensor is relayed to the temperature control means and adapted to effect the RF energy supply to the medical apparatus system.

6. The method of treating a tubular organ of a patient as in claim 1, the method further comprising the medical apparatus system having the RF energy delivery within the range of 50 to 2,000 kHz.

7. A method of treating a hemorrhoid of a patient, the method comprising the steps of:

(a) inserting a medical apparatus through the anal canal into the rectum of a patient, wherein the medical apparatus comprises a tubular shaft having a distal section, a distal end, a proximal end, and at least one lumen extending therebetween, wherein the distal section has at least one opening at one side of the tubular shaft; a handle attached to the proximal end of the tubular shaft, wherein the handle has a cavity; a deployable electrode assembly located inside one of the lumens of the tubular shaft at its distal section, wherein the electrode assembly comprises a concave-shaped shaft surface at the same side of the opening and a plurality of extendible wires shaped to form a cylindrical void when deployed, and wherein the plurality of wires are extended from the at least one opening at the distal section of the tubular shaft;

(b) deploying the electrode assembly to encircle the hemorrhoid; and (c) applying RF energy to the hemorrhoid encircled under the electrode assembly to effect treatment of the hemorrhoid.

8. The method of treating a hemorrhoid of a patient as in claim 7, the method further comprising the medical apparatus system having the shaft surface and the extendible wires for the cylindrical void being made of conductive material.

9. The method of treating a hemorrhoid of a patient as in claim 8, the method further comprising the medical apparatus system having a steering mechanism adapted for deflecting the distal section of the medical apparatus.

10. The method of treating a hemorrhoid of a patient as in claim 8, the method further comprising the medical apparatus system having the RF energy delivery within the range of 50 to 2,000 kHz.

11. The method of treating a hemorrhoid of a patient as in claim 7, the method further comprising at least one temperature sensor for the medical apparatus, wherein the temperature sensor is disposed at close proximity of the electrode assembly of the medical apparatus.

12. The method of treating a hemorrhoid of a patient as in claim 11, the method further comprising the medical apparatus system having a temperature control means, wherein the temperature measured from the temperature sensor is relayed to the temperature control means and adapted to effect the RF energy supply to the medical apparatus.

* * * * *